United States Patent
Gregoire et al.

[11] Patent Number: 5,964,716
[45] Date of Patent: Oct. 12, 1999

[54] METHOD OF USE FOR A MULTI-PORT BIOPSY INSTRUMENT

[75] Inventors: David K. Gregoire, Newport Coast, Calif.; Salvatore Privitera, West Chester; Edward Rhad, Fairfield, both of Ohio

[73] Assignee: Ethicon Endo-Surgery, Inc., Cincinnati, Ohio

[21] Appl. No.: 09/078,790

[22] Filed: May 14, 1998

[51] Int. Cl.$^6$ ...................................................... A61B 10/00
[52] U.S. Cl. ............................ 600/564; 600/566; 606/167
[58] Field of Search .................................... 600/562, 564, 600/565, 566, 567, 568; 606/167, 170, 181, 184, 185; 604/22

[56] References Cited

U.S. PATENT DOCUMENTS

| | | | |
|---|---|---|---|
| 3,512,519 | 5/1970 | Hall | 128/2 |
| 3,590,808 | 7/1971 | Muller | 128/2 B |
| 3,732,858 | 5/1973 | Banko | 128/2 B |
| 3,844,272 | 10/1974 | Banko | 128/2 B |
| 3,945,375 | 3/1976 | Banko | 128/6 |
| 4,651,753 | 3/1987 | Lifton | 600/564 |
| 4,799,495 | 1/1989 | Hawkins et al. | 128/754 |
| 4,819,635 | 4/1989 | Shapiro | 600/565 |
| 4,907,599 | 3/1990 | Taylor | 128/754 |
| 4,976,269 | 12/1990 | Mehl | 128/754 |
| 5,106,364 | 4/1992 | Hayafuji et al. | 604/22 |
| 5,125,413 | 6/1992 | Baran | 128/754 |
| 5,152,744 | 10/1992 | Krause et al. | 604/22 |
| 5,183,054 | 2/1993 | Burkholder et al. | 128/754 |
| 5,217,479 | 6/1993 | Shuler | 600/564 |
| 5,234,000 | 8/1993 | Hakky et al. | 600/564 |
| 5,284,156 | 2/1994 | Schramm et al. | 128/754 |
| 5,415,182 | 5/1995 | Chin et al. | 128/754 |
| 5,458,112 | 10/1995 | Weaver | 128/753 |
| 5,505,210 | 4/1996 | Clement | 600/566 |
| 5,526,822 | 6/1996 | Burbank et al. | 128/754 |
| 5,564,436 | 10/1996 | Hakky et al. | 128/754 |
| 5,649,547 | 7/1997 | Ritchart et al. | 600/566 |
| 5,669,394 | 9/1997 | Bergey et al. | 600/566 |
| 5,769,086 | 6/1998 | Ritchart et al. | 600/566 |
| 5,775,333 | 7/1998 | Burbank et al. | 600/567 |
| 5,823,970 | 10/1998 | Terwilliger | 600/567 |

*Primary Examiner*—Cary O'Connor
*Assistant Examiner*—Charles Marmor, II
*Attorney, Agent, or Firm*—Louis J. Capezzuto

[57] ABSTRACT

A method for using a surgical biopsy instrument for extracting a plurality of tissue samples from a body is disclosed. The instrument has a piercing needle that is initially inserted into the body. The needle has a piercing tip and a plurality of tissue receiving ports, for the reception of tissue samples, circumferentially arranged around the needle adjacent to the piercing tip. A first tissue sample is sampled at the first tissue receiving port and is removed from the instrument. A second tissue sample is sampled at a second tissue receiving port without moving the needle. The second tissue sample is removed from the body in the same manner as the first.

9 Claims, 9 Drawing Sheets

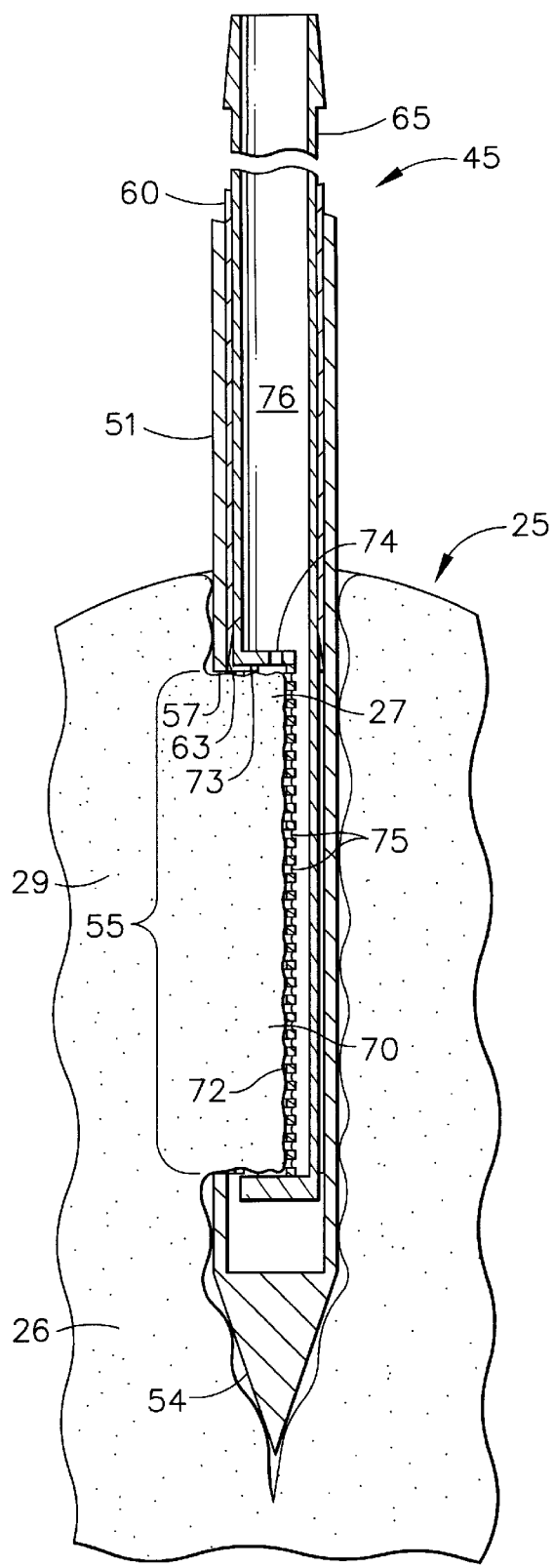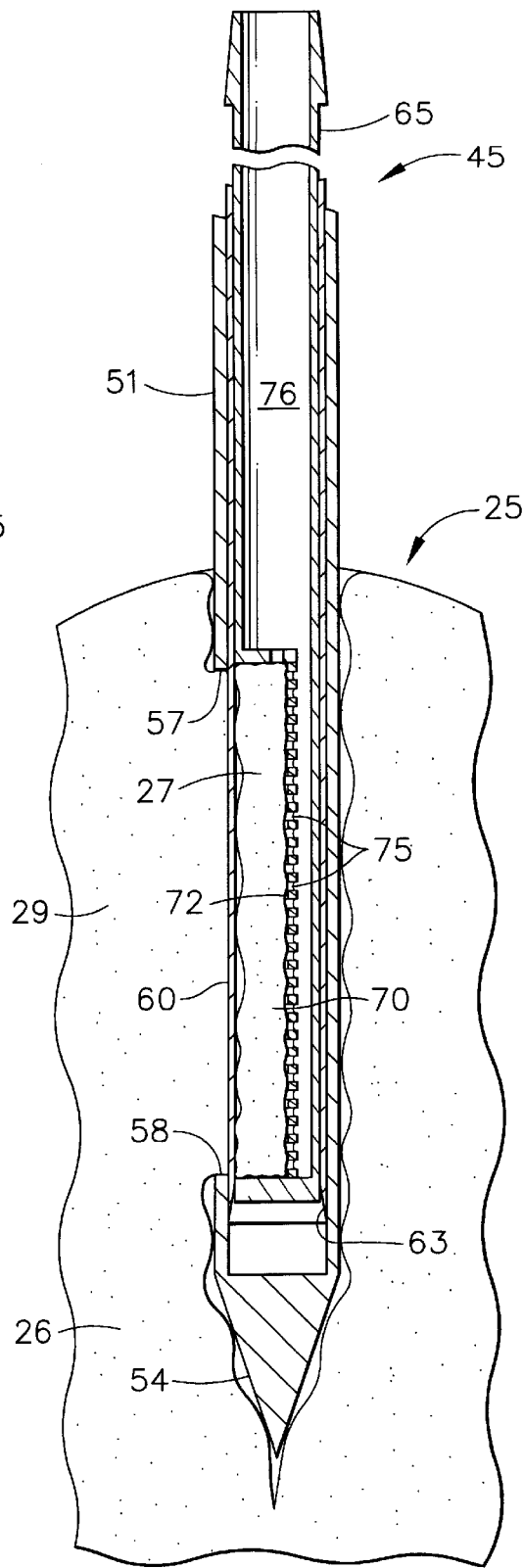
FIG. 10
FIG. 11

METHOD OF USE FOR A MULTI-PORT BIOPSY INSTRUMENT

FIELD OF THE INVENTION

The present invention relates, in general, to biopsy instruments and methods of taking biopsies, and more particularly, to instruments and methods for acquiring repeated subcutaneous biopsies in a minimally invasive manner.

BACKGROUND OF THE INVENTION

Biopsies are performed on human patients as a means of investigating a suspicious tumor, mass, or growth, on or within the patient. The tumor is identified by visual examination, palpitation, x-ray, MRI, ultrasound imaging, or other detection means. Once identified, there is a pressing need to rapidly evaluate the tumor as to whether it is malignant, or life threatening, or benign. This evaluation is generally performed by taking a biopsy. In a biopsy, a sample of tissue is removed from the patient and examined, usually under a microscope. Biopsies can be performed as an open or percutaneous procedure. With today's focus on women's breast cancer and the high mortality rate associated with this disease, there has been a tremendous effort to develop improved percutaneous methods of acquiring breast biopsies for analysis. If a cancer is detected and treated in the early stages of growth, there is a significant increase in the survival rate of the patient.

Percutaneous biopsies are usually performed with a needle-like instrument as a fine needle aspiration (FNA) or a core biopsy. The fine needle aspiration instrument retrieves a small amount of cells or cluster of cells that can be examined as a smear. In a core biopsy, a core of tissue is removed from the patient. It is important to note that the core biopsy method is attaining favor among physicians as it provides an intact tissue sample of the suspected area which makes it easier to properly diagnose the type, condition, and location of the suspected tissue mass.

The original core biopsy devices consisted of a coring needle, e.g. a hollow tube with a sharpened edge to obtain a plug of tissue. Such a device was inserted into the tumorous mass and withdrawn, sometimes without a core sample. Once the coring device was removed from the body, the plug of tissue was pushed out of the coring needle.

Whereas the coring needles did provide a tissue core, they were slow and had the additional disadvantage of removing a section of healthy breast tissue from the skin to the suspected cancerous site. If repeated tissue samples were required, the coring needle caused repeated trauma to the breast tissue from the repeated insertion and withdrawal of the needle through the tissue.

In response to the above deficiencies, an improved method of taking multiple biopsy samples was developed. The TRUE CUT® needle (sold by Travenol Laboratories, Deerfield, Ill.) provides the following advantages over the original core biopsy device or the use of hollow needles. First, the TRUE CUT® device has a pointed stylus that enables the device to penetrate the body to the surgical site without removing a core of healthy tissue. Second, the device uses an exterior sliding cutter tube that covers or shields the biopsy or tissue sample within the device as it is being withdrawn. To obtain a tissue sample, the TRUE CUT® needle depends upon the passive prolapse of tissue into a tissue receiving notch within the stylus. Once the tissue is prolapsed into the notch, the cutting tube is advanced to sever the tissue sample.

The above device was revolutionary in the field at the time because it only removed tissue samples from the desired surgical site and removed the sample from the body in an intact manner. However, the device still required multiple insertions and removals from the surgical site, which did not address the repeated tissue trauma issues. Additionally, size and shape of the tissue samples tended to be inconsistent. This may have been caused by the need for the tissue to passively prolapse into the device and by the forced migration of the tissue away from the cutter as it is advanced.

In response to the need for a method to acquire consistent tissue samples, the addition of vacuum to a biopsy device was created. The vacuum was applied to the tissue receiving chamber to draw the tissue within the chamber. This type of device offered consistent tissue sample size and held the tissue in place as the knife was advanced to sever the tissue. U.S. Pat. No. 3,590,808 to Wulf Muller discloses such a device.

Whereas the Muller device did address the need for vacuum to effectively hold the tissue in place to provide consistent samples, it did require an insertion and a removal of the device from the body for each tissue sample.

Another type of device is disclosed in U.S. Pat. No. 5,106,364 to Mineki Hayafuji et al. The Hayafuji et al. device uses suction to the tissue for drawing the tissue into an aperture or multiple apertures within the biopsy device. The multiple aperture biopsy device described by Hayafuji et. al. has multiple ports in a longitudinal orientation, e.g. the ports are linearly spaced along the longitudinal axis. Once the tissue is drawn or prolapsed into the aperture (or apertures), an internal cutting blade (or blades) is used to sever the tissue within the biopsy device. Once the tissue sample is sectioned, it is withdrawn from the instrument by the vacuum.

The Hayafuji et al. device was a breakthrough device in that: it did not need to be withdrawn and reinserted; provided multiple tissue samples in a short period of time; used vacuum to draw the tissue into the instrument for improved cutting; and withdrew the tissue samples out of the body. However, the Hayafuji at al. device was better suited for the removal of a tissue mass as it did not provide intact tissue samples for analysis. Additionally, the device produces multiple cut tissue samples which are not withdrawn from the body in an orderly manner, so the actual site location of the tissue sample is suspect at best.

Recognizing the shortcomings of the previous devices, an improved surgical biopsy device was developed and is disclosed in U.S. Pat. No. 5,526,822 to Burbank et al. The device is embodied in the MAMMOTOME® biopsy device (manufactured and sold by Ethicon Endo-Surgery, Inc., Cincinnati, Ohio). It is an automated surgical biopsy device that is inserted into a surgical site only once for removing multiple tissue samples through the use of vacuum to draw the tissue into the device. The vacuum is also used to hold the tissue while it is cut in order to provide elongated, intact tissue samples. This device includes an outer piercing needle with a single aperture port and an inner rotating tubular cutter that cuts tissue drawn into the single aperture port. The tissue is withdrawn from the surgical site within the tubular cutter and is ejected in a biopsy cage or cartridge for ease of identification. Additionally, the MAMMOTOME® device can be attached to a stereotactic table which provides visualization of the tissue site, via ultrasound or other visualization means, and provides precise movement of the device into the suspected surgical site.

It is important to note that, presently, the MAMMOTOME® device utilizes only one tissue port. Hence, multiple samples can be taken from the site in 360 degree fashion, by rotating the outer circumference of the piercing needle in order to position the aperture port at various locations around the circumference of the piercing needle.

Presently, there is no known a surgical biopsy device that can meet all of the needs outlined above, as well as provide a biopsy device that can provide tissue sampling at various locations around the outer circumference of the piercing needle without having to rotate the piercing needle in order to re-position the aperture port.

SUMMARY OF THE INVENTION

Accordingly, the present invention is a method for extracting a plurality of tissue samples from a body. The method comprises initially inserting a hollow piercing needle into the body. The needle has a piercing tip and a plurality of tissue receiving ports circumferentially arranged around the piercing needle adjacent to the tip.

A first tissue sample is sampled at a first tissue receiving port. Then the first tissue sample is removed from the instrument.

A second tissue sample is sampled at a second tissue receiving port without moving the hollow needle. The second tissue sample is removed from the instrument.

Additionally, since the present invention utilizes multiple tissue ports within the piercing needle, the multiple receiving ports negate the need to rotate the piercing needle within body tissue to reach body tissue around the outer circumference of the piercing needle. This reduces the possibility of the piercing needle twisting or binding the surrounding body tissue. The tissue extractor rotates within the piercing needle of the present invention to align with any one of the multiple receiving ports while obstructing the remaining ports. Once within alignment, the tissue sample is cut by advancing the cutter and removed by withdrawing the extractor. If a tissue sample is desired to be taken through another tissue receiving port, the tissue extractor is merely reinserted within the instrument and rotated into alignment with the detent of the desired tissue receiving port. The extractor has a configuration that permits one tissue port to be exposed or open while obstructing the non-selected tissue ports.

At least one vacuum opening within the tissue receptacle is utilized to connect and communicate with the tissue extractor with the extractor channel. The addition of vacuum to the tissue extractor draws the body tissue within the tissue receiving port, firmly holds the tissue sample in place against the tissue extractor during the cutting procedure, and holds the tissue sample in place during the removal of the tissue extractor from the cutter.

The piercing needle also has an alignment block that restricts the rotation of the probe when it is mounted within a probe driver. The probe driver attaches to a stereotactic table for the distal and proximal movement of the probe as it is inserted and withdrawn from body tissue, respectively.

The probe driver has a cutter drive mechanism for the rotation of the cutter when the cutter is mounted within the probe driver with the probe. The rotation of the cutting blade, as it is moved through tissue, produces a cleaner cut and a better biopsy sample for analysis.

A control unit which controls the application of vacuum to the tissue extractor is used to apply vacuum as it is required. Additionally, the control unit controls the rotation of the cutting blade during the cutting sequence. Additionally, the control unit can be used to: drive the motor to advance the cutting blade to sever the tissue sample; or drive motors within the stereotactic table to insert or withdraw the probe from the body.

The tissue extractor has a proximal wall, a distal wall, and a floor. The at least one opening in the extractor is provided in the floor of the tissue extractor for the passage of vacuum to the tissue extractor. The proximal wall of extractor has a vacuum orifice.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 10 is a side elevational view, in cross section, of the distal end of the probe of the surgical biopsy instrument of FIG. 1, wherein the probe has penetrated into the body tissue, the cutter has been moved to a proximal-most position, and a vacuum has been applied, drawing a tissue sample into the probe;

FIG. 11 is a side elevational view, in cross section, of the distal end of the probe of the surgical biopsy instrument of FIG. 1, wherein the probe has penetrated into the body tissue, the vacuum is still applied, and the cutter has been returned or moved back to the distal-most position severing a tissue sample within;

DETAILED DESCRIPTION OF THE INVENTION

Figure 1:
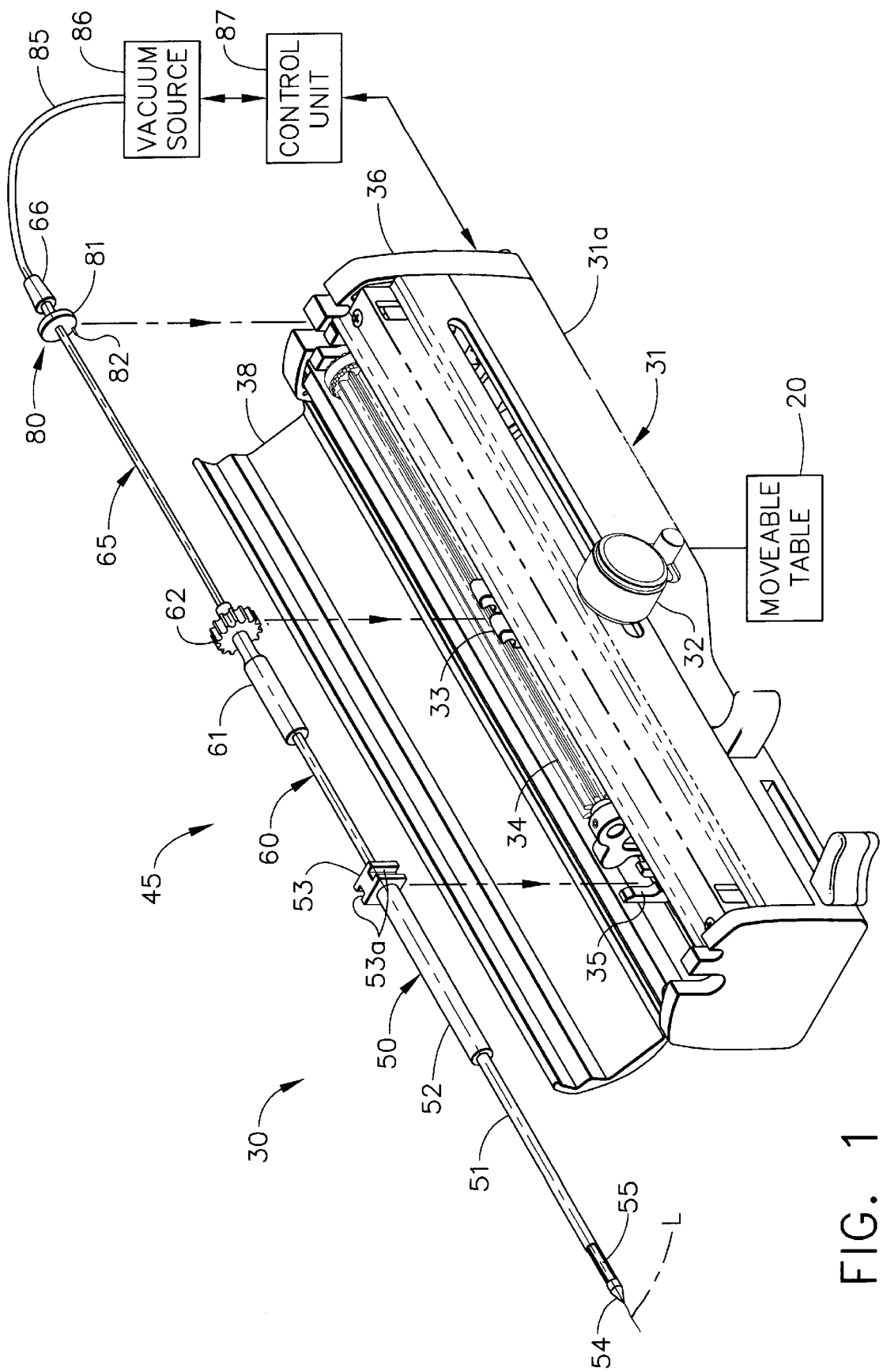
FIG. 1 is an exploded isometric view of a surgical biopsy instrument of the present invention.

As best shown in FIG. 1., the present invention is a surgical biopsy instrument 30 that is a minimally invasive type instrument for acquiring repeated subcutaneous biopsies. The surgical biopsy instrument 30 has a multi-port probe 45 having at least one port 55 for insertion into a human body 25 (FIG. 8) for extraction of a biopsy or tissue sample 27 (FIG. 11) therefrom.

The multi-port probe 45 of the surgical biopsy instrument 30 is removably mounted to a powered probe driver 31. The probe driver 31 is attached to a moveable table 20 such as a stereotactic guidance system (not shown) for moving the multi-port probe 45 distally in order to pierce the body 25 and as well as proximally in order to remove the multi-port probe 45 from the body. A vacuum source 86 is attached to the proximal end of the multi-port probe 45 by a vacuum line 85 for the delivery of a vacuum to the multi-port probe 45. A control unit 87 is used to control the sequence of actions performed by the surgical biopsy instrument 30 in order to obtain a biopsy sample or tissue sample 27 from the body 25. The control unit 87 controls the movement of; the motorized stereotactic table, the application of vacuum to the multi-port probe 45, and activates the cutter motor (not shown) within the probe driver 31.

Figure 2:
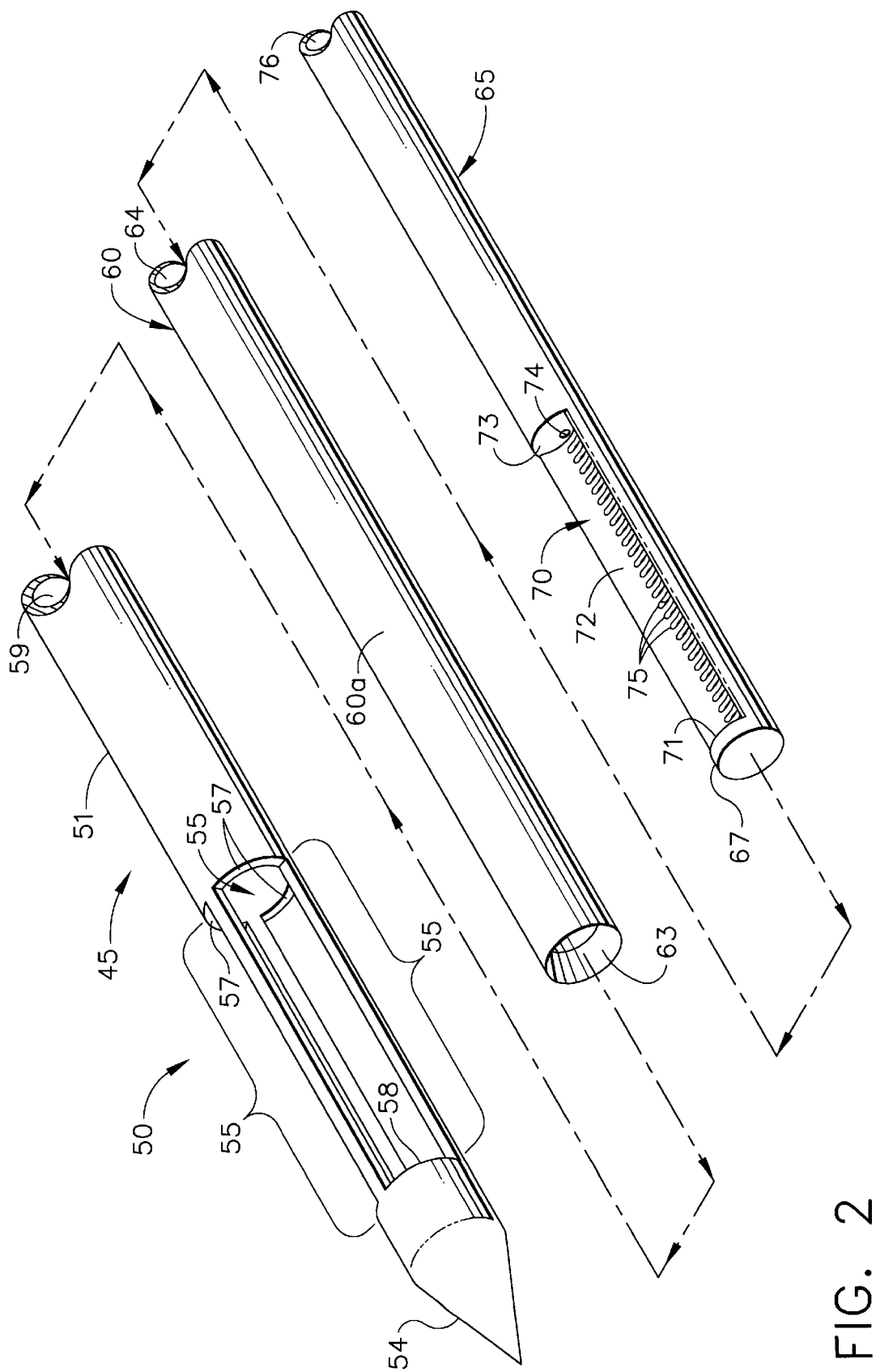
FIG. 2 is an exploded isometric view of the distal ends of the components of a probe of the surgical biopsy instrument of FIG. 1.

The multi-port probe 45 has three components; a piercing probe 50 having a elongated hollow piercing needle 51 for piercing the body 25, a cutter 60 for cutting the tissue sample 27, and a tissue extractor 65 for the extraction of the tissue sample 27 from the body 25. As shown in FIG. 2, the components of the probe are assembled by the insertion of the distal end of the tissue extractor 65 into the proximal end of the cutter 60 and insertion of the distal end of the cutter into the proximal end of the piercing probe 50. Each of the components are shown in a partially inserted condition prior to the mounting of the multi-port probe 45 into the probe driver 31 (FIG. 1). Each one of these components interfaces or mates with a portion of the probe driver 31 as described below.

The probe driver 31 includes a housing 31a having a moveable cover 38 hingedly attached thereto. Within the housing 31a there is a housing mount fork 35 for receiving the piercing probe 50, a cutter advance fork 33 for receiving the cutter 60, and an elongated driver gear 34 to mate with and rotate the cutter 60. The housing 31a also includes a back plate 36 to mate with the tissue extractor 65. A cutter advance knob 32 is movably positioned on the driver 31 for providing rapid advancement and retraction of the cutter 60. Longitudinal movement of the cutter advance knob 32 rapidly advances and retracts the cuter 60 within the multi-port probe 45. The cutter advance knob 32 is rotated during the tissue sample 27 cutting sequence in order to provide a slower rate of advancement of the cutter 60. This slower manual advancement produces a cleaner cut and a more intact tissue sample 27. Actuation of the knob 32 moves both the cutter advance fork 33 and the cutter 60 proximally and distally respectively.

The piercing probe 50 consists of the hollow piercing needle 51 attached to a probe housing 52 and an alignment mount 53. The hollow piercing needle 51 extends the full length of the piercing probe 50 and has a distal piercing tip 54 for the penetration of tissue, an open proximal end, and a needle passageway 59 extending therebetween for reception of the cutter 60 and the tissue extractor 65 therein. Adjacent to the piercing tip 54, there is at least one tissue receiving port 55. A first embodiment of the piercing probe 50 includes three equally spaced tissue receiving ports 55 interconnected with the needle passageway 59 for the reception of tissue samples 27 therein as best shown in FIG. 2. The tissue receiving ports 55 are elongated apertures for the retrieval of a sizable localized tissue sample 27. The ports 55 have proximal port edges 57 and distal port edges 58. The use of multiple receiving ports 55 eliminates the need to rotate the piercing needle 51 within the body 25 and eliminates any potential twisting and binding of the surrounding body tissue 26 that could occur with rotation of the piercing needle 51. The use of the multiple ports 55 allows for the sampling of multiple tissue samples 27 from a tissue site 29 (FIG. 9) in a 360 degree fashion without having to rotate the piercing needle 51.

As shown in FIG. 1, the alignment mount 53 is attached at the distal end of the piercing needle 51. The alignment mount 53 holds the receiving ports 55 in a fixed angular orientation about the longitudinal axis "L" of the piercing probe 50. A pair of alignment slots 53a are located on the lateral portions or sides on the alignment mount 53 for mating and aligning the piercing needle 51 to the housing mount fork 35 in the probe driver 31. It is important to note that once the probe 50 is mated to the probe driver 31, the probe 50 cannot be rotated about the longitudinal axis and the receiving ports 55 are aligned in a preferred orientation.

As shown in FIG. 2, the elongated tubular cutter 60 is slidable and rotatable within the needle passageway 59 of the piercing needle 51. The cutter 60 has an elongated hollow cutter tube 60a with a cutter bore 64 extending the entire length of the cutter 60. A cutting blade 63 is located on the distal end of the hollow cutter tube 60a. The cutter 60 also has a cutter body 61 and a cutter gear 62 adjacent to the proximal end of the cutter 60 as shown in FIG. 1. The cutter gear 62 mates with the cutter advance fork 33 and the elongated driver gear 34 in the probe driver 31. As the cutter advance fork 33 moves the cutter 60 proximally and distally within the probe driver 31, the cutter gear 62 remains engaged with the elongated driver gear 34. The driver gear 34 is driven by the motor (not shown) in the probe driver 31 to rotate the cutter 60 as directed by the control unit 87.

The innermost component of the multi-port probe 45 is the tissue extractor 65, which is slidably and rotatably mounted within the cutter bore 64 of the cutter 60 (FIG. 2) and removably positioned within the multi-port probe 45. The tissue extractor 65, is a hollow tubular structure having a closed distal end plate 67 and a generally concave tissue receptacle 70 adjacent to the distal end as illustrated in FIG. 2. An extractor channel 76 extends from the proximal face of the distal end plate 67 to the open proximal end of the extractor 65.

Figure 3:
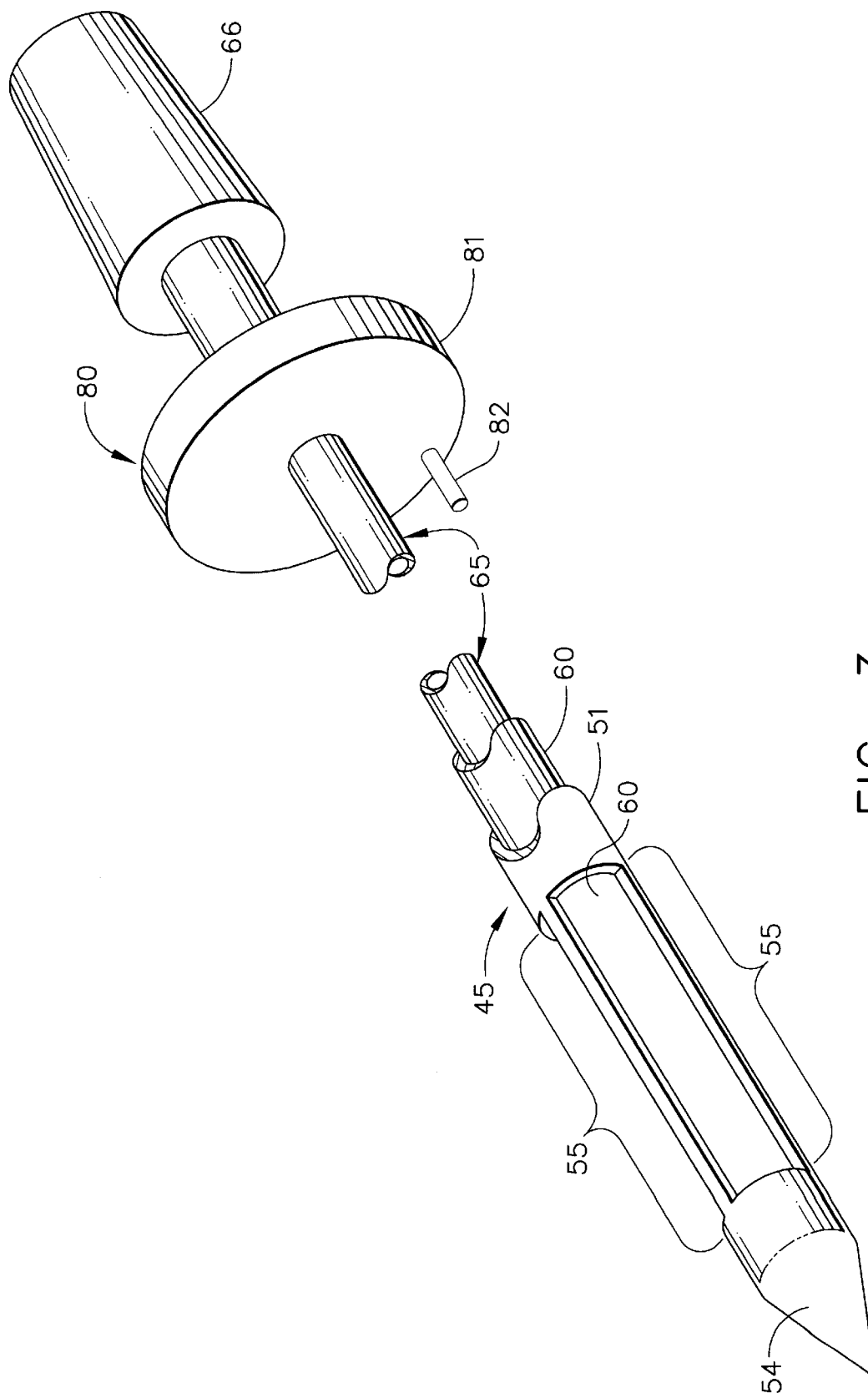
FIG. 3 is an enlarged isometric view of the proximal and distal ends of the probe of the surgical biopsy instrument of FIG. 1.

Referring now to FIGS. 1–3, a vacuum connector 66 is located at the proximal end for the attachment of the vacuum line 85 to the extractor channel 76 for the delivery of vacuum thereto as best shown in FIG. 1. The vacuum from the vacuum source 86 can be turned on and off as required by the control unit 87. A detent 80 is located at the proximal end of the extractor 65 adjacent to the vacuum connector 66. The detent 80 has a detent knob 81, and a distally extending detent pin 82 or detent member. The detent pin 82 has a specific angular orientation with the tissue receptacle 70 which will be discussed later. The tissue extractor 65 is rotatable within the piercing needle 51 to position the tissue receptacle 70 behind any tissue receiving port 55 in the piercing needle 51 for the reception of tissue samples 27 therein.

The tissue receptacle 70 is concave and is defined by the outer diameter of the distal end plate 67, a distal wall 71 of the distal end plate 67, a concave floor 72, and a proximal wall 73 for the reception of tissue samples 27 therein. The tissue receptacle 70 has a series of evenly spaced vacuum openings 75 within the floor 72 that interconnect and communicate with the tissue extractor channel 76. A proximal orifice 74 is located within the proximal wall 73 and also interconnects and communicates with the tissue extractor channel 76. As mentioned above, vacuum is applied uninterrupted to the tissue extractor channel 76 and the tissue receptacle 70 through the openings 75 and the orifice 74 for drawing tissue samples 27 through the receiving port 55 and into the tissue receptacle 70.

FIG. 3 shows the coaxial placement of the tissue extractor 65 within the cutter 60 and the cutter 60 within the piercing needle 51 to make the multi-port probe 45. The cutter 60 is shown fully inserted into the piercing needle 51 so that the receiving ports 55 are closed by the cutter 60.

Figure 4:
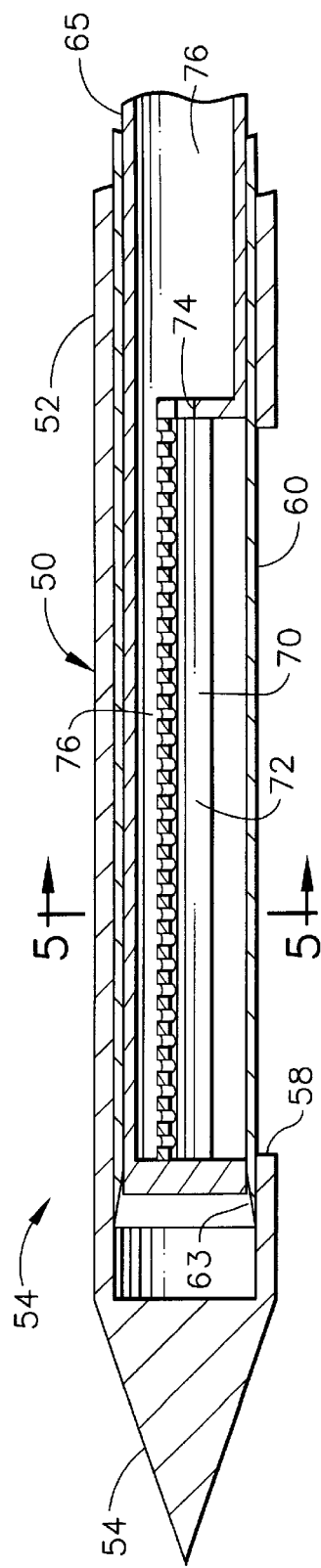
FIG. 4 is a side elevational view, in cross section, of the probe of the surgical biopsy instrument of FIG. 1.

In FIG. 4, the distal end of the probe 55 has been sectioned along the longitudinal axis to show the components. The cutting blade 63 of the cutter 60 is shown in the most distal position, referred to henceforth as the first position, such that the cutting blade 63 is located distal to distal port edge 58 of the piercing tip 54. The tissue receptacle 70 is shown aligned with one of the tissue receiving ports 55. The extractor channel 76 reduces from a circular cross section as shown on the right to a crescent-shaped passageway underneath the floor 72 of the tissue receptacle 70.

Figure 5:
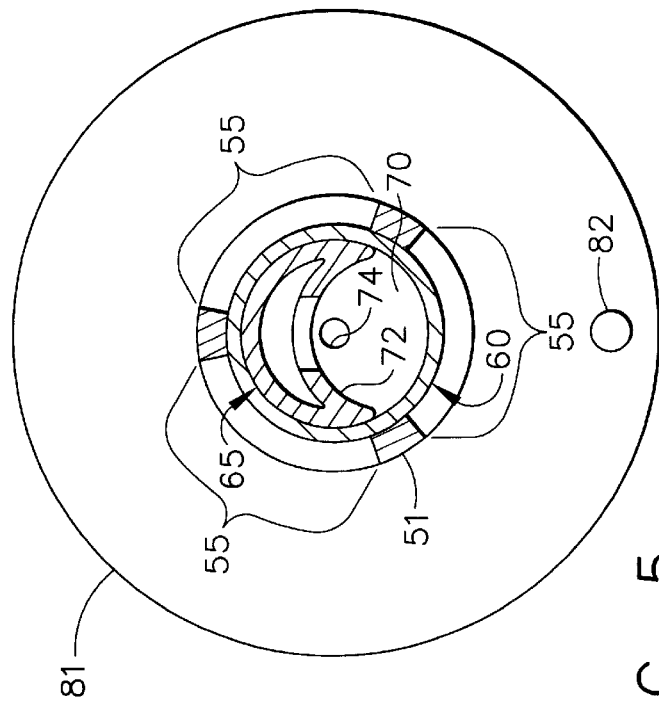
FIG. 5 is a cross section of the probe of FIG. 4 along line 5—5.

FIG. 5 shows a section view of the distal end of the multi-port probe 45 of FIG. 4, along the line 5—5. The section is taken across the multiple receiving ports 55 located in the piercing needle 51. As shown, the cutter 60 is in the first or distal-most position and has closed off the tissue receiving ports 55. The following components have been removed from this view for clarity: the probe housing 52, the alignment mount 53, the cutter body 61, and the cutter gear 62. This view better illustrates the alignment of the detent pin 82 with the tissue receptacle 70. The tissue receptacle 70, located adjacent to the distal end of the tissue extractor 65, is shown aligned with the lowermost tissue receiving port 55. The detent pin 82, located near to the proximal end of the tissue extractor 65, is also aligned with the lowermost tissue receiving port 55. It is important to note that when the detent pin 82 is aligned with one of the receiving ports 55, the tissue receptacle 70 is also aligned with the same receiving port 55 while at the same time obstructing the remaining two receiving ports 55. The crescent cross section of the tissue extractor channel 76 is clearly shown. Whereas the cutter is shown as a tubular structure that closes off all the ports, it is possible to use a multi port cutter such that the cutting blade 60 is moveably disposed with respect to, and covers only the tissue receiving port 55 that is in alignment with the tissue receptacle 70.

Figure 6:
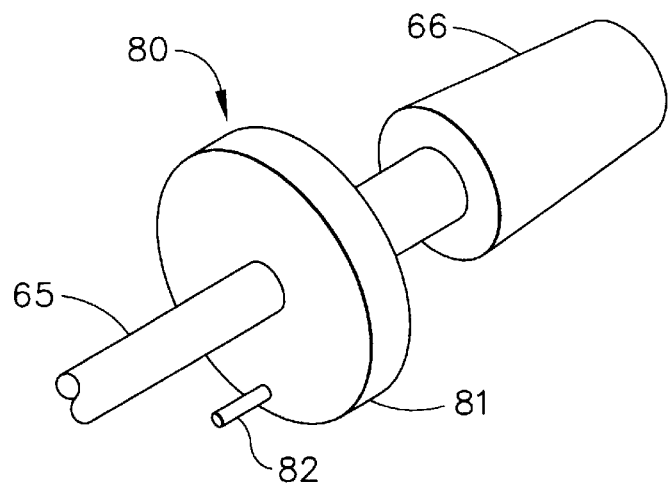
FIG. 6 is an enlarged isometric view of the proximal end of a tissue extractor of the surgical biopsy instrument of FIG. 1.
Figure 7:
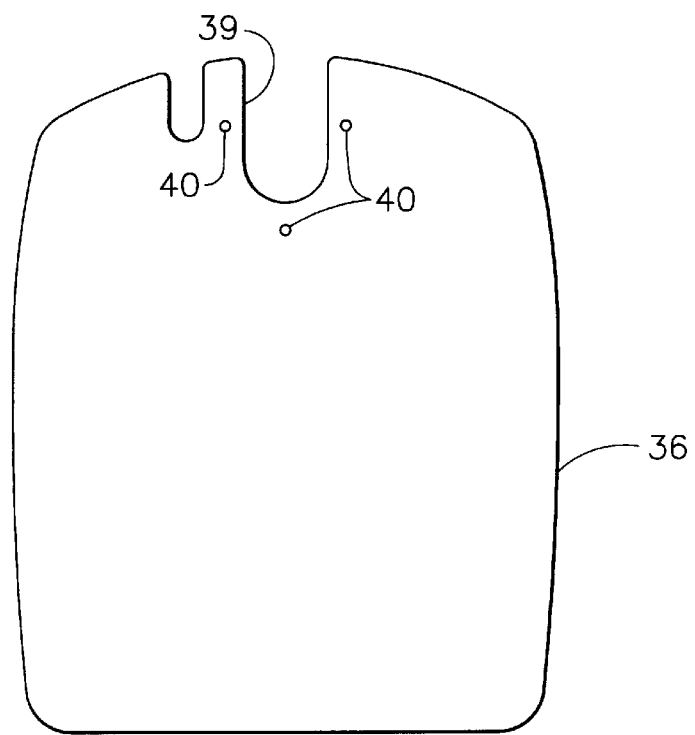
FIG. 7 is an elevational view of the proximal side of a back plate of the surgical biopsy instrument of FIG. 1.

Referring now to FIG. 6, the detent pin 82 extends distally from the indexing knob 80 adjacent to the distal end of the tissue extractor 65. FIG. 7 shows the proximal face of the back plate 36 of the probe driver 31. A series of detent holes 40 are shown in a specific angular orientation around the probe slot 39. When the multi-port probe 45 is installed within the probe driver 31, the detent 80 is used by the operator to fully place the detent pin 82 into one of the detent holes 40. This action places the tissue receptacle 70 into alignment with one of the receiving ports 55 while blocking the remaining ports 55 with distal end of the extractor 65. The detent pin 82 also functions as an indicator to inform the user of the sector or receiving port 55 from which the tissue samples 27 will be taken.

FIGS. 8–13 best illustrate the method of use according to the present invention. The surgical biopsy device 30 (FIG. 1) is used to obtain multiple biopsy samples from a surgical site within a patient's body 25. The patient is generally positioned upon a surgical table (not shown) and is given a local anesthetic to anesthetize the desired penetration site. The surgical biopsy device 30 is attached to a moveable table 20, such as a stereotactic table, and is moved into an approximate position above the body 25.

Figure 8:
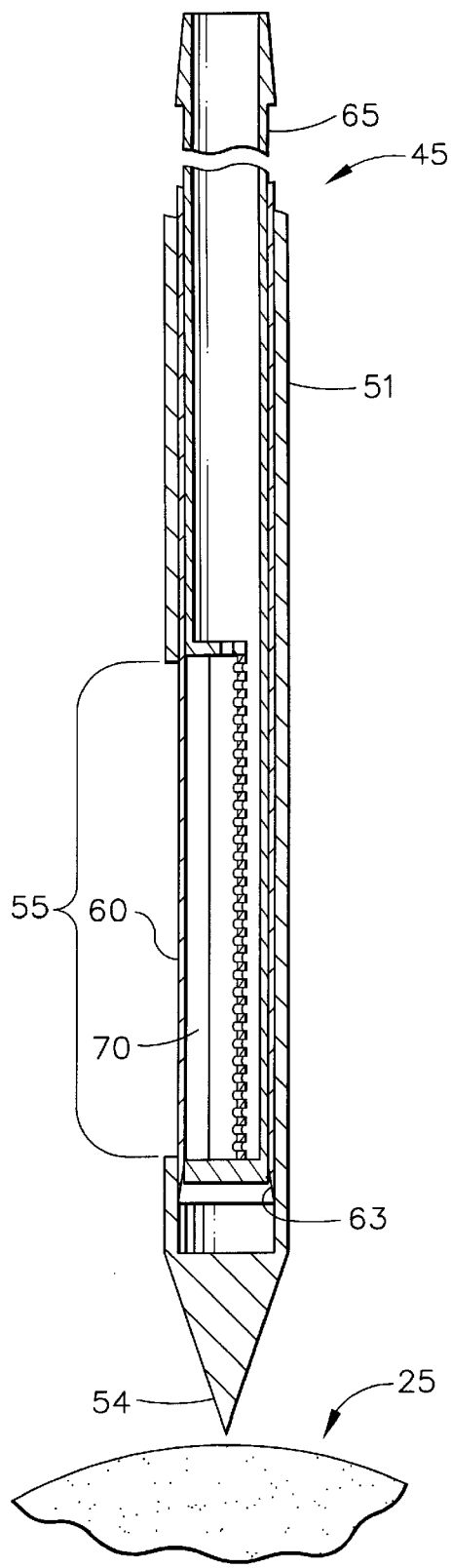
FIG. 8 is a side elevational view, in cross section, of the of the distal end of the probe of the surgical biopsy instrument of FIG. 1 wherein the probe is poised above a body prior to penetration.
Figure 9:
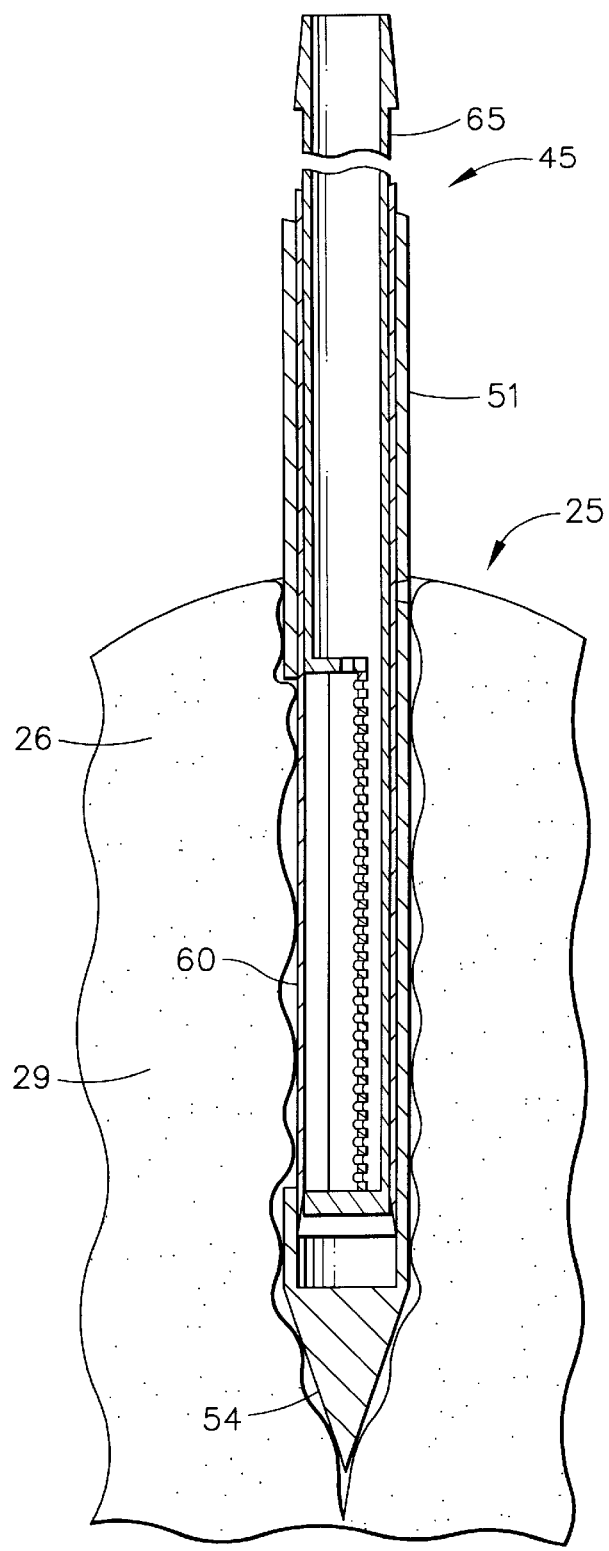
FIG. 9 is a side elevational view, in cross section, of the distal end of the probe of the surgical biopsy instrument of FIG. 1, wherein the probe has penetrated into body tissue and a cutter is in a distal-most position.

As shown in FIG. 8, the position of the multi-port probe 45 undergoes fine adjustment above the body using the moveable table 20 (FIG. 1), prior to the insertion of the piercing needle 51 into the body 25. The tissue extractor 65 is positioned within the multi-port probe 45 to place the tissue receptacle 70 in alignment with one of the receiving ports, for instance, the left hand tissue receiving port 55. Accordingly, the distal end of the extractor 65 obstructs the remaining two receiving ports 55 which will cause vacuum to be drawn and directed to the non-obstructed tissue port 55, in this example, the left hand receiving port 55 (FIG. 5). Thus, tissue samples 27 can only be withdrawn into the tissue receptacle 70 through this non-obstructed port 55 when the cutter 60 is moved to it's proximal most position. Prior to insertion, the cutting blade 63 is moved to the first or most distal position in order to close the tissue receiving ports 55 with the cutter 60. piercing needle 51 is advanced into the body 25 by distal movement of the moveable table 20. As best illustrated in FIG. 9, the piercing tip 54 is advanced until the tissue ports 55 reach the required depth at the tissue site 29. The body tissue 26 presses inwardly upon the multi-port probe 45 and is shown partially prolapsed into the tissue receiving ports 55. The prolapsed tissue 26, within the tissue receiving ports 55, is in contact with the exterior of the cutter 60 where the exterior of the cutter 60 is exposed at the open tissue receiving ports 55. However, the prolapsed tissue 26 is blocked from entering the tissue extractor 70. The tissue extractor 65 and the cutter 60 are still in the same position, e.g. in the distal-most position relative to the piercing needle 51 as also shown in FIG. 6.

Referring now to FIG. 10, the cutting blade 63 of the cutter 60 is moved proximally from the first, or distal-most position to a second position, e.g. a position near the proximal port edge 57 of the receiving port 55, henceforth described as the second position. When the cutter 60 is in the second position, it exposes the distal end of the tissue receptacle 70 to the open tissue receiving port 55. As shown, the tissue receptacle 70 is aligned with the left tissue receiving port 55 for the reception of body tissue 26 into the tissue receptacle 70. The control unit 87 actuates the vacuum source 86 to deliver vacuum to the extractor channel 76 of the tissue extractor 65. The tissue receptacle 70 is connected to the extractor channel 76 by the vacuum openings 75 in the floor 72 of the tissue extractor and by the proximal orifice 74 in the proximal wall 73. The application of vacuum to the extractor channel 76 of the tissue extractor 65 causes the tissue sample 27 of the body tissue 26 to ptosis or prolapse, drawing the prolapsed tissue sample 27 into the receiving port 55 and into the tissue receptacle 70 as shown. The prolapsed tissue sample 27 is securely held within the tissue receptacle 70 by the uninterrupted vacuum delivered through the vacuum openings 75 and the proximal orifice 74. Since the other receiving ports 55 are obstructed by the distal end of the extractor 65, tissue samples 27 are only taken through the selected port 55, i.e. the port 55 directly aligned with the tissue receptacle 70.

As shown in FIG. 11, the prolapsed tissue sample 27 is then severed from the tissue site 29 by the advancement of the cutting blade 63 from its second position near to the proximal port edge 57 to the first position distal to the distal port edge 58. The advancement of the cutting blade 63 closes the tissue receiving ports 55 with the cutter tube 60a. Prior to the advancement of the cutting blade 63, the control unit 87 activates the motor (not shown ) within the probe driver 31 to rotate the driver gear 34, the cutter gear 62 and the cutting blade 63 (FIG. 1). The rotating cutting blade 63 is advanced distally to the first position in order to sever the tissue sample 27. This is accomplished by the rotation of the cutter advance knob 32 by the user. The tissue sample 27 is tightly held within the tissue receptacle 70 by the application of vacuum to the extractor channel 76. This enables the user to cut the securely held tissue sample 27 without twisting and distortion. The tissue sample 27 is now ready for removal from the body 25 by the tissue extractor 65. The vacuum actively holds the tissue sample 27 in a fixed position within the tissue receptacle 70 as the tissue extractor 65 is removed or extracted from the multi-port probe 45. The continuous application of vacuum to the tissue sample 27 ensures the collection of a fully intact and undistorted tissue sample 27 for analysis.

Figure 12:
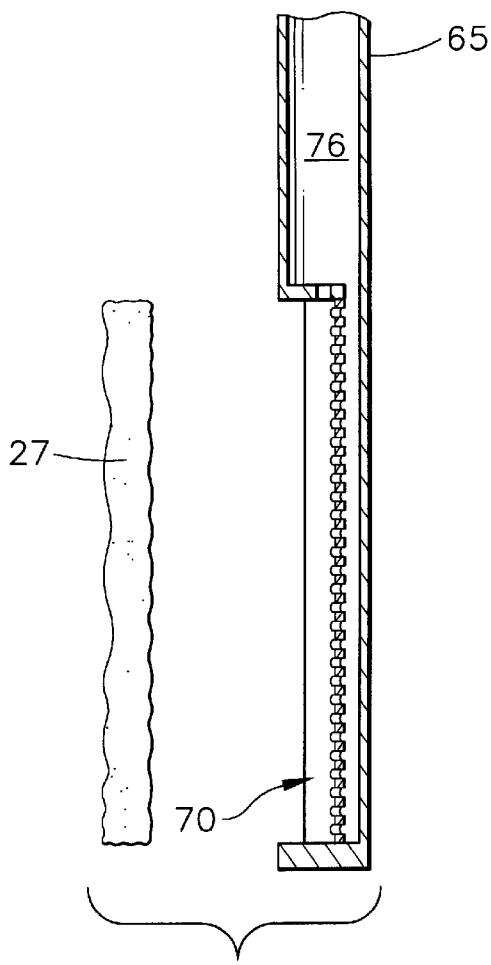
FIG. 12 is a side elevational view, in cross section, of the distal end of a tissue extractor of the surgical biopsy instrument of FIG. 1, wherein the tissue extractor has been removed from the probe, the vacuum has been turned off and the tissue sample is shown extracted from the body.

The tissue sample 27 is securely held within the extracted tissue extractor 65 until the user elects to release the sample 27 from the tissue extractor by the deactivation of vacuum to the extractor channel 76. As shown in FIG. 12, the vacuum is deactivated and tissue sample 27 is separated from the tissue extractor and ready for analysis. While not critical to the present invention, the vacuum supplied by the vacuum source 86 can be released manually or under the control of the control unit 87 to release the intact and undistorted tissue sample 27 from the tissue extractor 65.

Figure 13:
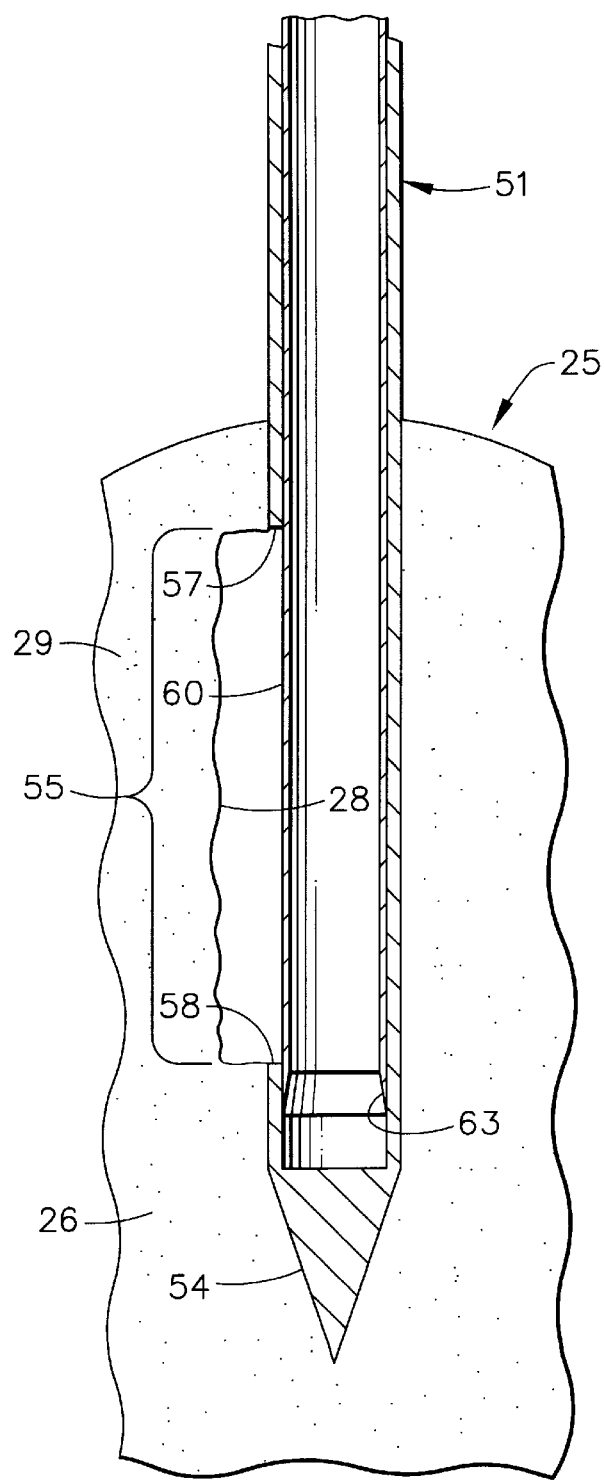
FIG. 13 is a side elevational view, in cross section, of the distal end of the probe of the surgical biopsy instrument of FIG. 1, wherein the probe remains in the body tissue, and the tissue extractor has been removed for the extraction of the tissue sample from the surgical site.

Referring now to FIG. 13, a view of the distal end of the piercing needle 51 and cutter 60 is shown with the remaining components in position at the tissue site 29 for the removal of the next tissue sample 27. A void 28 is left at the position from where the tissue sample 27 was removed. Additional tissue samples can be removed from the same port 55, .e.g. the left port 55 if desired. Alternatively, the tissue extractor 65 is then rotated upon reinsertion to one of the other ports 55 for removal of additional tissue samples 27 around the outer circumference of the piercing needle 51, e.g. in 360 degree fashion, without the trauma associated with frequent removal or rotation of the piercing probe 50 to obtain multiple tissue samples 27 from the tissue site 29. If desired, the samples can be taken in a range less than or equal to 360° around the circumference of the needle 51. The same steps as outlined above are followed in order to withdraw other tissue samples 27 from other receiving ports 55, e.g. one of the other two receiving ports 55 instead of the left port 55. Thus, the use of a piercing needle 51, with multiple tissue receiving ports 55 located adjacent to the piercing tip 54, offers distinct access and trauma reduction advantages in the retrieval of multiple tissue samples 27 from the tissue site 29.

Figure 14:
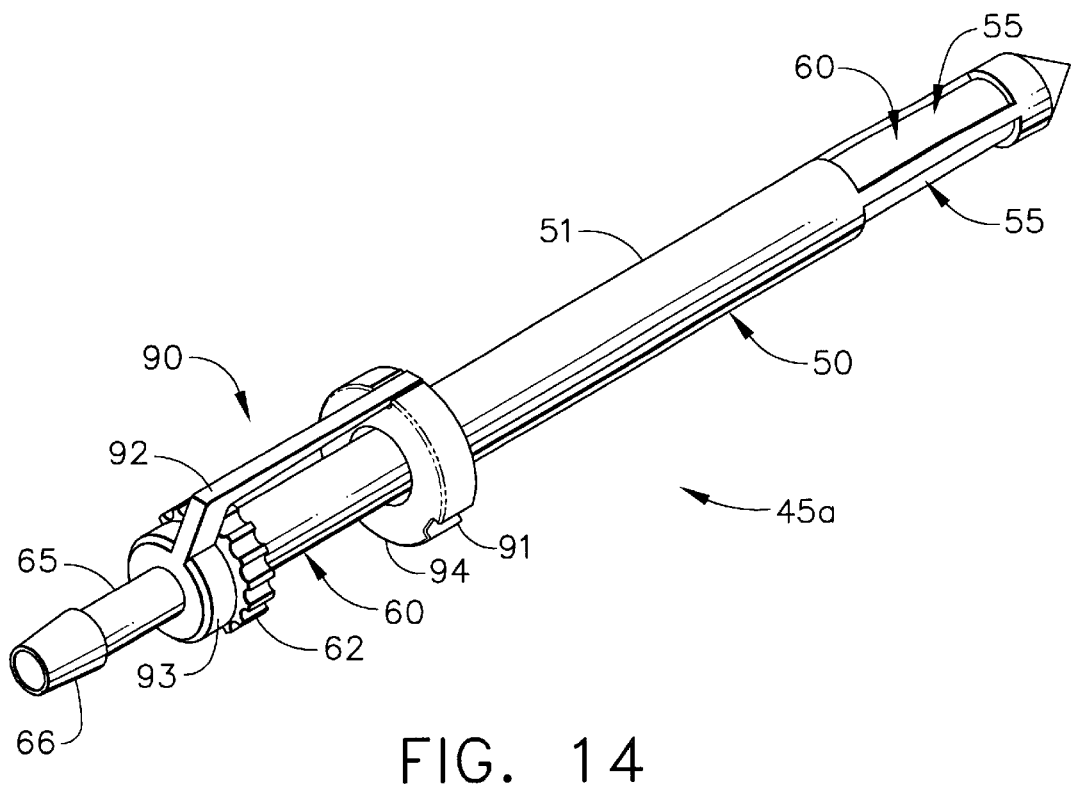
FIG. 14 is an isometric view of an alternate embodiment of the surgical biopsy instrument having a blade detent mechanism.

Turning now to FIG. 14, an alternate embodiment is shown of a probe 45a. The same reference numerals are used to designate like parts to the multi-port probe 45 embodied in FIGS. 1–13. Probe 45a is a hand held instrument for the removal of tissue samples 27 from the body 25.

The piercing probe 50 of the probe 45a has a piercing needle 51 extending the full length of the piercing probe 50 and a detent blade 92 or detent member near the proximal end. A blade extractor disk 94 is fixedly attached to the proximal end of the piercing needle 51. Detent receptacles 91 are equally spaced around the periphery of the disk 94 and are in direct alignment with the receiving ports 55 of the piercing needle 51. The piercing probe 50 is held in one of the operator's hands during operation.

The cutter gear 62 attached to the distal end of the cutter 60 rotates and moves the cutting blade 63 (FIG. 2) from the first position to the second position. Likewise, cutter gear 62 moves the cutting blade 63 from the second position to the first-position in reverse motion of the cutter gear 62 by the user. The cutter 60 is operated by the hand not holding the piercing probe 50.

The blade detent mechanism 90 includes a blade body 93 having an elongated deflectable detent blade 92 that extends outwardly and distally from the blade body 93. The distal end of the detent blade 92 is received within one of the indexing receptacles 91 for the alignment of the tissue receptacle 70 (FIG. 4) with one of the receiving ports 55 on the distal end of the probe 45a. With the piercing needle 51 firmly held in one hand, the blade body 93 and the detent blade 92 are rotated to another detent receptacle 91 to position the distal tissue receptacle 70 behind the desired, respective receiving port 55. The detent blade 92 is a spring member and holds the detent blade within the detent receptacle 91. The vacuum connector 66 is located on the distal end of the tissue extractor 65 for connection to the vacuum line 85 and a vacuum source 86 as depicted in FIG. 1. Whereas the blade detent mechanism 90 described above is used with a hand held probe 45a, the blade detent mechanism 90 can also be used with any other probe such as the previously described multi-port probe 45 for use on a probe driver 31.

As described above, the method of use of the probe 45a device as depicted in FIG. 14 is manual and operated without the use of the driver 31 (FIG. 1). The sequence whereby a tissue sample 27 is removed is the same method as generally depicted in FIGS. 8–13. However, the vacuum must be manually activated to obtain a tissue sample as shown in FIGS. 10, 11, and 12.

Figure 15:
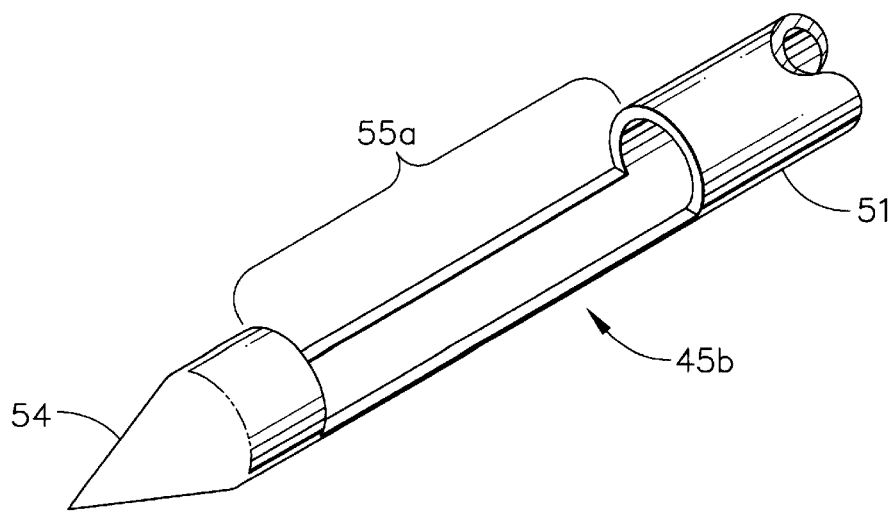
FIG. 15 is an isometric view of yet another alternate embodiment of a surgical biopsy instrument of the present invention having a single port with a large width.

FIG. 15 shows another embodiment of the present invention wherein a probe 45b has a single receiving port 55a. The cutter 60 and tissue extractor 65 operate in the same manner described above for the retrieval of multiple tissue samples 27. It should be noted that the width of the single receiving port 55a is larger than the width of receiving ports 55 on the multi-port probe 45 of FIG. 1. This receiving port 55a defines an opening in the needle 51 ranging from approximately 15° to approximately 330° and preferably ranging from approximately 180° to approximately 270° . This enables the tissue receptacle 70 of the tissue extractor to be rotated throughout a wide angular band within the width of the single receiving port 55a for the reception of tissue samples 27 therein.

Another embodiment of the method according to the present invention allows for the cutter to be moved to the second position prior to insertion. Thus, in this second embodiment, the multi-port probe 45 is inserted with the cutter 60 in the second position. In this insertion configuration, the tissue extractor 65 covers all but one of the multiple tissue receiving ports 55.

It is within the scope of this invention, in an alternate embodiment, to fix the tissue extractor in it's distal most position such that it can be rotated about the longitudinal axis to any port yet cannot be removed from the piercing probe 50. Such an instrument would work well with a single or a multi-port probe 45. Referring now to FIGS. 4 and 5, this alternate embodiment enables the operator to rotate the tissue extractor to any tissue receiving port 55 while blocking the non-selected tissue receiving ports 55, if applicable.

The proximal orifice 74 communicates with the extractor channel 76 (FIG. 4) and supplies vacuum to the tissue receptacle. By enlarging this orifice 74, or removing the proximal wall 73 (FIG. 2), tissue samples can be removed from the piercing probe 50 by the application of vacuum. Referring now to FIG. 10, the application of vacuum to the tissue extractor 65, draws tissue into the tissue receiving port 55 and into the tissue receptacle 70. As shown in FIG. 11, the cutter 60 is moved to the distal most position to cut the tissue sample 27 as shown. The continuing application of vacuum to the extractor channel 76 draws the tissue sample 27 into the proximal orifice 74 or through the opening created by the removed proximal wall 73, and into the extractor channel 76. Once the sample is in the channel 76, it is drawn out of the probe 45 by the continuing application of vacuum. Once the sample is out of the probe 45, it can be captured for examination.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for extracting a plurality of tissue samples from a body, said method comprising the steps of:
    a) inserting a hollow needle into said body, said needle having a piercing tip and a plurality of tissue receiving ports circumferentially arranged around said piercing needle adjacent to said tip;
    b) sampling a first tissue sample at a first tissue receiving port;
    c) removing said first tissue sample from said instrument;
    d) sampling a second tissue sample at a second tissue receiving port without moving said hollow needle; and
    e) removing said second tissue sample from said instrument.

2. The method according to claim 1, including providing a tissue extractor with said needle and taking said first tissue sample and said second tissue sample by applying a vacuum to a tissue extractor to draw said first tissue sample and said second tissue sample into said tissue extractor through said first tissue receiving port and said second tissue receiving port respectively.

3. The method according to claim 2, further including providing a cutter with said needle and moving said cutter across said tissue receiving ports for cutting said tissue sample.

4. The method according to claim 1, further comprising: sampling additional tissue samples from said tissue receiving ports around the circumference of said piercing needle in a range from approximately 30° to approximately 360°.

5. A method of using a surgical biopsy instrument for extracting tissue samples from a body, said method comprising the steps of:
    a) inserting a hollow piercing needle into said body, said needle having a piercing tip and a plurality of tissue receiving ports circumferentially arranged around said needle adjacent to said tip;
    b) aligning a tissue extractor with a first tissue receiving port of said needle;
    c) sampling a first tissue sample at said first tissue receiving port;
    d) removing said first tissue sample from said instrument while said piercing needle remains in said body;
    e) aligning said extractor with a second tissue receiving port; and
    f) sampling a second tissue sample at said second tissue receiving port.

6. The method according to claim 5, including removing said second tissue sample from said instrument.

7. The method according to claim 6, further comprising: taking said first tissue sample and said second tissue sample by applying a vacuum to said instrument.

8. The method according to claim 7, further comprising: sampling said first said tissue sample and said second tissue sample by cutting said first and said second tissue samples.

9. The method according to claim 5, further comprising: sampling additional tissue samples from said tissue receiving ports around the circumference of said piercing needle in a range from approximately 30° to approximately 360°.

* * * * *